(12) United States Patent
Terada et al.

(10) Patent No.: US 11,905,361 B2
(45) Date of Patent: *Feb. 20, 2024

(54) BASE PROLIFERATING AGENT, AND BASE-REACTIVE RESIN COMPOSITION CONTAINING SAID BASE PROLIFERATING AGENT

(71) Applicant: Nippon Kayaku Kabushiki Kaisha, Tokyo (JP)

(72) Inventors: Kiwamu Terada, Tokyo (JP); Hirokazu Kuwabara, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/851,401

(22) Filed: Jun. 28, 2022

(65) Prior Publication Data

US 2022/0332886 A1   Oct. 20, 2022

Related U.S. Application Data

(63) Continuation of application No. 16/975,425, filed as application No. PCT/JP2019/006979 on Feb. 25, 2019, now Pat. No. 11,401,370.

(30) Foreign Application Priority Data

Feb. 26, 2018   (JP) ................................. 2018-031507

(51) Int. Cl.
   *C08G 59/50*   (2006.01)
   *C07D 213/75*   (2006.01)
   *G03F 7/038*   (2006.01)

(52) U.S. Cl.
   CPC ......... *C08G 59/506* (2013.01); *C07D 213/75* (2013.01); *G03F 7/038* (2013.01)

(58) Field of Classification Search
   CPC .................................................... C07D 213/75
   See application file for complete search history.

(56) References Cited

U.S. PATENT DOCUMENTS

| | | |
|---|---|---|
| 3,220,846 A | 11/1965 | Tinker et al. |
| 4,060,420 A | 11/1977 | Merkel et al. |
| 4,511,650 A | 4/1985 | Hirai et al. |
| 4,560,763 A | 12/1985 | Sato et al. |
| 4,639,418 A | 1/1987 | Yabuki et al. |
| 2008/0070154 A1 | 3/2008 | Taguchi |
| 2008/0200580 A1 | 8/2008 | Aoki et al. |
| 2012/0178027 A1 | 7/2012 | Chen et al. |
| 2017/0293225 A1 | 10/2017 | Arimitsu et al. |

FOREIGN PATENT DOCUMENTS

| | | |
|---|---|---|
| GB | 998949 | 7/1965 |
| GB | 1470451 | 4/1977 |

(Continued)

OTHER PUBLICATIONS

Makiuchi et al., "Differences between Aminopyridine Derivatives and Imidazole as Basic Initiator of Curing Reaction of Epoxy Resin", Journal of Network Polymer, Japan, 2012, pp. 323-327, vol. 33:6.

*Primary Examiner* — Megan McCulley
(74) *Attorney, Agent, or Firm* — The Webb Law Firm

(57) ABSTRACT

This base proliferating agent is represented by formula (1) or (2), where, in formula (1) and (2), R1, R2, and R3 independently represent a hydrogen atom or a substituent and n independently represents an integer from 1 to 4. A base-reactive resin composition can include this base proliferating agent and a base-reactive compound.

(Continued)

(1)

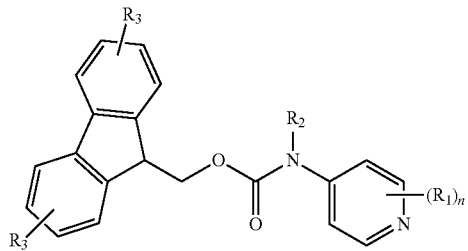

(2)

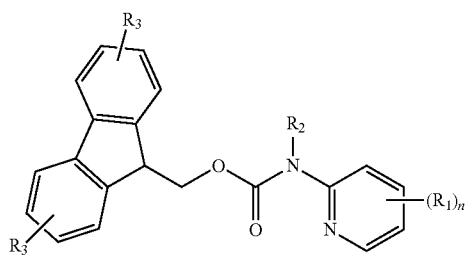

4 Claims, 2 Drawing Sheets

(56) References Cited

FOREIGN PATENT DOCUMENTS

| JP | S5022625 | | 3/1975 |
|---|---|---|---|
| JP | S59157637 | A | 9/1984 |
| JP | S59168440 | A | 9/1984 |
| JP | 59180537 | A | 10/1984 |
| JP | S59195237 | A | 11/1984 |
| JP | S6132844 | A | 2/1986 |
| JP | S6151139 | A | 3/1986 |
| JP | S6151140 | A | 3/1986 |
| JP | S6152638 | A | 3/1986 |
| JP | S6153634 | A | 3/1986 |
| JP | S6153640 | A | 3/1986 |
| JP | S6155644 | A | 3/1986 |
| JP | S6155645 | A | 3/1986 |
| JP | 2000330270 | A | 11/2000 |
| JP | 2002128750 | A | 5/2002 |
| JP | 2006282657 | A | 10/2006 |
| JP | 2008081720 | A | 4/2008 |
| JP | 2014115643 | A | 6/2014 |
| JP | 2014185303 | A | 10/2014 |
| JP | 5733618 | B2 | 6/2015 |
| JP | 2015214608 | A | 12/2015 |
| JP | 6156875 | B2 | 7/2017 |
| WO | 9721678 | A1 | 6/1997 |
| WO | 0127085 | A1 | 4/2001 |
| WO | 2014185303 | A1 | 11/2014 |
| WO | 2016052493 | A1 | 4/2016 |

BASE PROLIFERATING AGENT, AND BASE-REACTIVE RESIN COMPOSITION CONTAINING SAID BASE PROLIFERATING AGENT

CROSS-REFERENCE TO RELATED APPLICATIONS

This application is a continuation of U.S. patent application Ser. No. 16/975,425, filed Aug. 25, 2020, which is the United States national phase of International Application No. PCT/JP2019/006979 filed Feb. 25, 2019, and claims priority to Japanese Patent Application No. 2018-031507 filed Feb. 26, 2018, the disclosures of which are hereby incorporated by reference in their entirety.

BACKGROUND OF THE INVENTION

Technical Field

This present invention relates to a base proliferating agent, and a base-reactive resin composition containing a base proliferating agent. More particularly, the instant invention relates to a base proliferating agent which can disintegrate by the action of a base to produce another base, a base-reactive resin composition containing the base proliferating agent.

Background Art

The photosensitive resin composition containing an acid generator generating an acid by light irradiation are used as a photoresist material or a photocurable material.

In the photosensitive resin composition, the acid produced from an acid generator acts as a catalyst or a polymerization initiator. For example, when the photosensitive resin composition containing an acid generator is used as a photoresist material, the change of the solubility of a resin component by chemically modifying the resin component due to a strong acid produced from an acid generator is used to form a pattern.

For such photoresist materials, the formation of a pattern having high etching resistance in addition to high resolution and sensitivity, particularly, the formation of a pattern having high resistance to oxygen plasma etching as a deep UV photoresist material is required. However, combination of a photoacid generator with a resin material is limited to some extent, and therefore, the new photosensitive system without using any acid generator is demanded.

Meanwhile, various studies are conducted for improving the a photocuring rate of a monomer, an oligomer or a polymer. A material used in radical photopolymerization system where some vinyl monomers are polymerized by using radical species as an initiator generated by the action of light has been widely studied. Also, a material used in cationic polymerization system where an acid generated by the action of light works as catalyst has been studied actively. However, in case of a material used in radical polymerization system, because oxygen in the air suppresses the polymerization reaction (cure reaction), specific ingenuity for blocking oxygen is needed. In case of a material used in cationic polymerization system, there is no suppression with oxygen. However, a strong acid produced from a photoacid generator remains in the cured product after curing. Therefore, corrosion or property modification of resin due to the strong acid may be occurred.

From these backgrounds, a photosensitive resin composition having high resolution and high sensitivity, being capable of forming a pattern having high etching resistance, not effected by curing inhibition with oxygen in the atmosphere, and containing no corrosive substance such as a strong acid is strongly demanded.

As one of the means for solving problems described above, a method using a polymerization reaction or a chemical reaction with a base catalyst, for example, a method using a photosensitive resin composition having properties that a resin is chemically changed by a base produced with action of light as a catalyst is studied. On the other hand, by using the properties that the compound having an epoxy group causes cross-linking reaction by the action of a base, a method including producing amines to be used as a initiator or a catalyst in an epoxy resin layer by action of light or heat and then conducting heat treatment to obtain a cured product is proposed. However, even when the amines are used as an initiator or a catalyst, a curing rate of epoxy compound is low. In order to sufficiently cure the resin composition, long time is needed. Therefore, heat treatment at a high temperature is needed so that the curing ratio can be increased.

In order to solve these problems, a photosensitive resin composition where a base proliferating agent secondarily amplifying a base generated by the action of light is combined with a photobase generator and a base-reactive compound is studied. Patent Literature 1 and 2 disclose a photosensitive composition containing a urethane compound which is a base proliferating agent causing a base proliferating reaction. Also, Patent Literature 3 to 7 disclose various base proliferating agents.

An imidazole derivative is generally used for curing an epoxy resin. An aminopyridine derivative having a curing ratio which is higher than the curing ratio of the imidazole derivative not only has a short pot life but also is difficult to control the reaction, when the aminopyridine derivative is mixed with the epoxy resin. Therefore, the aminopyridine derivative is not often used (Non-Patent Literature 1).

CITATION LIST

Patent Literature

Patent Literature 1: JP 2000-330270 A
Patent Literature 2: JP 2002-128750 A
Patent Literature 3: JP 2014-115643 A
Patent Literature 4: JP 2015-214608 A
Patent Literature 5: JP 5,733,618 B
Patent Literature 6: JP 6,156,875 B
Patent Literature 7: WO 2014/185303 A

Non-Patent Literature

Non-Patent literature 1: "Network polymer" Vol. 33 No. 6 (2012)

SUMMARY OF INVENTION

Technical Problem

The present invention was made in view of the above problems. One of the objects of the present invention is to provide a base proliferating agent having operatability improved by making aminopyridines latent by derivation of the aminopyridines which could not been used in, for example, a cross-linking reaction of epoxy compounds, because of high active of the aminopyridines; and a base-reactive resin composition containing the base proliferating agent.

Solution to Problem

By earnest research, the present inventors of found that a base proliferating agent having a specific structure where aminopyridines are made latent by derivation of the amino-pyridines can be used in, for example, a cross-linking reaction of epoxy compounds as well as can effectively proceed with the base proliferating reaction where new base is generated in the presence of a base so as to finish the present invention.

That is, the present invention relates to the followings:
[1] A base proliferating agent having formula (1) or (2):

wherein in formula (1) and (2), $R_1$, $R_2$ and $R_3$ are each independently a hydrogen atom or a substituent, and n is each independently an integer of 1 to 4;
[2] The base proliferating agent according to the above [1], wherein $R_1$ is each independently a hydrogen atom, an alkyl group having a carbon number of 1 to 6, an aryl group having a carbon number of 6 to 12, a halogen atom, a nitro group, a nitroso group or a cyano group, or $R_1$ is connected to each other to form a ring; wherein $R_2$ is each independently a hydrogen atom an alkyl group having a carbon number of 1-6 or an aryl group having a carbon number of 6 to 12, and wherein $R_3$ is each independently a hydrogen atom, an alkyl group having a carbon number of 1 to 6, an aryl group having a carbon number of 6 to 12 or a halogen atom.
[3] A base-reactive resin composition comprising the base proliferating agent according to the above [1] or [2] and a base-reactive compound.
[4] The base-reactive resin composition according to the above [3], wherein the base-reactive compound is at least one selected from a group consisting of an epoxy compound, a silicon compound and an oxetane compound.
[5] The base-reactive resin composition according to the above [3] or [4], further comprising a base generator.
[6] The base-reactive resin composition according to the above [5], wherein the base generator is a thermal base generator.
[7] The base-reactive resin composition according to the above [5], wherein the base generator is a photobase generator.
[8] A cured product of the base-reactive resin composition according to any one of the above [3] to [7].

Effects of Invention

The base proliferating agent represented by the formula (1) obtained by making aminopyridines latent by derivation of the aminopyridines can be used in, for example, a cross-linking reaction of epoxy compounds as well as can effectively proceed with the base proliferating reaction where another base is newly generated in the presence of a base. Therefore, the base proliferating agent can be suitably used for a base-reactive resin composition which can be cured by the action of light or heat.

DESCRIPTION OF THE INVENTION

The present invention is described below in detail.
<Base Proliferating Agent>
The base proliferating agent of the present invention is represented by following formula (1) or (2).

In formulas (1) and (2), $R_1$, $R_2$ and $R_3$ are each independently a hydrogen atom or a substituent, and n is each independently an integer of 1 to 4. $R_1$ plurally existing may be connected to each other to form a ring.

The substituent represented by $R_1$ is not particularly limited, but is preferably an alkyl group having a carbon number of 1 to 6, an aryl group having a carbon number of 6 to 12, a halogen atom, a nitro group, a nitroso group or a cyano group. That is, $R_1$ in formulas (1) and (2) is preferably each independently a hydrogen atom, an alkyl group having a carbon number of 1 to 6, an aryl group having a carbon number of 6 to 12, a halogen atom, a nitro group, a nitroso group or a cyano group. $R_1$ plurally existing may be the same or different from each other.

The substituent represented by $R_2$ is not particularly limited, but is preferably an alkyl group having a carbon number of 1 to 6, or an aryl group having a carbon number of 6 to 12. That is, $R_2$ in formulas (1) and (2) is preferably each independently a hydrogen atom, an alkyl group having a carbon number of 1 to 6, or an aryl group having a carbon number of 6 to 12.

The substituent represented by $R_3$ is not particularly limited, but is preferably an alkyl group having a carbon number of 1 to 6, an aryl group having a carbon number of 6 to 12, or a halogen atom. That is, $R_3$ in formulas (1) and (2) is preferably each independently a hydrogen atom, an alkyl group having a carbon number of 1 to 6, an aryl group having a carbon number of 6 to 12 or a halogen atom. Two of $R_3$ existing in formula (1) may be the same or different from each other. Two of $R_3$ existing in formula (2) may be the same or different from each other.

Examples of an alkyl group having a carbon number of 1 to 6 represented by $R_1$, $R_2$ and $R_3$ in formulas (1) and (2) include a linear or branched alkyl group such as methyl group, ethyl group, n-propyl group, iso-propyl group, n-butyl group, iso-butyl group, sec-butyl group, t-butyl group, n-pentyl group and n-hexyl group, and a cyclic alkyl group such as cyclopropyl group, cyclobutyl group, cyclopentyl group and cyclohexyl group. The alkyl group is preferably an alkyl group having a carbon number of 2 to 6, more preferably a linear or branched alkyl group having a carbon number of 2 to 6.

Examples of an aryl group having a carbon number of 6 to 12 represented by $R_1$, $R_2$ and $R_3$ in formulas (1) and (2) include a phenyl group, a naphthyl group and a tolyl group. The aryl group is preferably an aryl group having a carbon number of 6 to 10.

Examples of a halogen atom represented by $R_1$ and $R_3$ in formula (1) and (2) include a fluorine atom, a chlorine atom, a bromine atom and an iodine atom.

The ring formed by connecting plural $R_1$ to each other is not particularly limited, but examples of the ring include a five-membered ring or a six-membered ring such as benzene ring, naphthalene ring, furan ring, pyrrole ring, imidazole ring, thiophene ring, pyrazole ring, oxazole ring, thiazole ring, pyridine ring and pyrazine ring, and benzene ring is preferable.

Preferably, $R_1$ in formulas (1) and (2) is each independently a hydrogen atom, an alkyl group having a carbon number of 1 to 6 or a cyano group, or is connected to each other to form a benzene ring; more preferably $R_1$ is each independently a hydrogen atom, an alkyl group having a carbon number of 1 to 6 or a cyano group; and further preferably $R_1$ is a hydrogen atom.

Preferably, $R_2$ in formulas (1) and (2) is each independently a hydrogen atom or an alkyl group having a carbon number of 1 to 6; and more preferably $R_2$ is a hydrogen atom.

Preferably, $R_3$ in formulas (1) and (2) is each independently a hydrogen atom or an alkyl group having a carbon number of 1 to 6; and more preferably $R_3$ is a hydrogen atom.

Next, the synthesis method of the base proliferating agent represented by formula (1) or (2) of the present invention will be explained.

The base proliferating agent represented by formula (1) or (2) of the present invention can be synthesized by a well-known method, for example, using the reaction of chloride derivative of fluorene with an aminopyridine derivative described below. Specifically, 9-fluorenylmethyl chloroformate is reacted with 4-aminopyridine at room temperature, and then the obtained solution is washed by water to produce the compound represented by formula (1) or (2), which is in line with the chemical flow described below. As a purification method, a crystallization method is suitable, because the crystallization method can produce a compound obtained by the synthesis method has high crystallinity, but the purification can also be conducted by washing with solvent.

The specific examples of the base proliferating agent represented by formula (1) or (2) are shown as the formulas (A) to (I) described below, but the present invention is not limited thereto.

(A)

(B)

(C)

(D)

(E)

(F)

(G)

(H)

(I)

The base proliferating agent has characteristics capable of generating new bases by decomposition of the base proliferating agent by the action of base. The bases for action are preferably the same as the bases newly generated from the proliferating agent. Therefore, by action of a small amount of a base to the base proliferating agent of the present invention, the base proliferating agent can generate a larger amount of the base corresponding to the total amount of the base proliferating agent by decomposing self-proliferatively.

Then a base-reactive resin composition of the present invention is explained. The base-reactive resin composition of the present invention contains the base proliferating agent represented by formula (1) or (2) and a base-reactive compound causing curing reaction by the presence of base as an essential component.

The content of the base proliferating agent in the base-reactive resin composition of the present invention is usually 0.01 to 10% by mass, preferably 0.05 to 5% by mass to the base-reactive compound which is described below. One kind of the base proliferating agent represented by formula (1) or (2) may be used alone in the base-reactive resin composition of the present invention, and two or more kinds of the base proliferating agent may be used in combination.

In the base-reactive resin composition of the present invention, additional base proliferating agent other than the base proliferating agent represented by formula (1) or (2) may be used together, as long as the advantageous effects of the present invention are not damaged. As long as the additional base proliferating agent which can be used together is well known, the additional base proliferating agent is not particularly limited, but is preferably a base proliferating agent which is excellent in the compatibility with the base-reactive compound described below. The ratio of the base proliferating agent represented by formula (1) or (2) to the total of base proliferating agents contained in the base-reactive resin composition of the present invention is preferably 50% by mass or more, more preferably 70% by mass or more.

The base-reactive compound contained in the base-reactive resin composition of the present invention is a compound which reacts by the action of the base generated by the base proliferating agent or the base generator described below which is an optional component of the base-reactive resin composition to conduct the curing by cross-linking. As a base-reactive compound, an epoxy compound having at least one epoxy group, a silicon compound having at least one alkoxysilyl group or silanol group, or an oxetane compound including an oxetane ring are preferably used. The examples include the compounds of No. 2-1 to 6-4 described below. The base-reactive compound may be used alone or in combination of two or more.

The above epoxy compound (epoxy resin) having at least one epoxy group is not limited as long as the epoxy compound is the compound having one or more epoxy groups. Examples include diglycidyl ether, ethyleneglycoldiglycidyl ether, glycerindiglycidyl ether, propyleneglycoldiglycidyl ether, butanedioldiglycidyl ether, diethyleneglycoldiglycidyl ether, glycerolpolyglycidyl ether, diglycerolpolyglycidyl ether, sorbitolpolyglycidyl ether, allylglycidyl ether, butylglycidyl ether, phenylglycidyl ether, alkylphenolglycidyl ether, polyethyleneglycoldiglycidyl ether, tripropyleneglycoldiglycidyl ether, neopentylglycoldiglycidyl ether, 1,6-hexanedioldiglycidyl ether, glycerinpolyglycidyl ether, diglycerinpolyglycidyl ether, trimethylolpropanepolyglycidyl ether, cresylglycidyl ether, aliphatic diglycidyl ether, multifunctional glycidyl ether, tertiary fatty acid mono glycidyl ether, Spiro glycoldiglycidyl ether and glycidylpropoxytrimethoxy silane. Those epoxy compounds may be halogenated or hydrogenated and a derivative of those epoxy compounds may be used as the above epoxy compound. Those epoxy compounds may be used alone or in combination of two or more in the base-reactive resin composition of the present invention.

Examples of the above silicon compound (silicon resin) having at least one alkoxysilyl group or silanol group include alkoxysilane compound and silane coupling agent.

Examples of alkoxysilane compound include trimethylmethoxy silane, dimethyldimethoxy silane, methyltrimethoxy silane, tetramethoxy silane, methyldimethoxy silane, trimethylethoxy silane, dimethyldiethoxy silane, methyltriethoxy silane, tetraethoxy silane, diphenyldimethoxy silane, phenyl trimethoxy silane, diphenyldiethoxy silane, phenyltriethoxy silane, hexyltrimethoxy silane, tetrapropoxy silane and tetrabutoxy silane. Those alkoxysilane compounds may be used alone or in combination of two or more for the base-reactive resin composition of the present invention.

Examples of the silane coupling agent include vinyl silane, acryl silane, epoxy silane, and amino silane. Examples of the vinyl silane include vinyl trichlor silane, vinyltris (β-methoxyethoxy) silane, vinyltriethoxy silane and vinyltrimethoxy silane. Examples of the acrylsilane include γ-metacryloxypropyl trimethoxy silane and γ-metacryloxypropyl methyl dimethoxy silane. Examples of the epoxy silane include β-(3, 4-epoxycyclohexyl) ethyltrimethoxy silane, γ-glycidoxypropyltrimethoxy silane and γ-glycidoxypropylmethyldiethoxy silane. Examples of the amino silane include N-β-(aminoethyl)-γ-aminopropyltrimethoxy silane, N-β-(aminoethyl)-γ-aminopropylmethyldimethoxy silane, γ-aminopropyltrimethoxy silane and N-phenyl-γ-aminopropyltrimethoxy silane. Other silane coupling agent include γ-mercaptopropyltrimethoxy silane, γ-chloropropylmethyldimethoxy silane and γ-chloropropylmethyldiethoxysilane. Those silane coupling agents may be used alone or in combination of two or more for the base-reactive resin composition of the present invention.

Examples of the above oxetane compound (oxetane resin) including oxetane ring include a monomer oxetane compound and a dimer oxetane compound. Examples of the oxetane compound include 4,4'-bis [(3-ethyl-3-oxetanyl) methoxymethyl]biphenyl, 1,4-benzene dicarboxylic acid bis [(3-ethyl-3-oxetanyl)methyl]ester, 1,4-bis [(3-ethyl-3-oxetanyl)methoxymethyl]benzene, 3-ethyl-3-(((3-ethyloxetane-3-yl)methoxy)methyl)oxetane (also called 3-(((3-ethyloxetane-3-yl)methoxy)methyl)-3-ethyloxetane), 3-ethylhexyl oxetane, 3-ethyl-3-hydroxyoxetane, 3-ethyl-3-hydroxymethyl oxetane, and oxetanic phenol novolac. Those oxetane compounds may be used alone or in combination of two or more for the base-reactive resin composition of the present invention.

The specific examples of the base-reactive compound are given below. It is noted that in the polymer (base-reactive compound) of compounds No. 2-1 to 2-8, the compounds No. 2-1 to 2-5 are base-reactive compounds causing reactions of elimination and decarboxylation by the action of base, and compounds No. 2-6 to 2-8 are base-reactive compounds causing elimination reaction by the action of base to produce a carboxylic acid.

2-1

2-2

2-3

2-4

2-5

3-1

2-6

2-7

3-2

2-8

3-3

3-4

It is noted that all base reactive compounds No. 2-1 to 2-8 form a polymer group which causes an elimination reaction by the action of base and undergoes polarity conversion, and the base-reactive compound can be used as a material (resist material) performing patterning by using the change of solubility before and after decomposition.

Other examples of the base-reactive compound are given below. In the base-reactive compounds of No. 3-1 to 3-4, the material (mixture) of compound No. 3-1 causes the reactions of dehydration condensation and cross-linking by the action of base. The material (mixture) of compound No. 3-2 also causes the reaction of dehydration condensation and cross-linking by the action of base. The material (polymer) of compound No. 3-3 causes the reaction of decarboxylation by the action of base. The material of compound No. 3-4 causes the reaction of the imide formation by the action of base. X in compound No. 3-1 and No. 3-2 is a number which is more than 0 and 1 or less.

In the base-reactive resin composition of the present invention, an epoxy compound having at least one epoxy group can be used as a base-reactive compound. By reacting an epoxy compound having at least two or more epoxy groups with the base, ring-opening polymerization of the epoxy group can be conducted to produce the polymer. Furthermore, the addition of a base to an epoxy compound can modify the epoxy compound chemically. The examples of the epoxy compounds (compounds No. 4-1 to 4-9) are given below.

4-1

4-2

4-3

4-4

4-5

4-6

4-7

4-8

4-9

Other examples (compounds No. 4-10 to 4-12) of the epoxy compound (polymer) are given below.

4-10

4-11

A silicon compound having at least one silanol group or alkoxysilyl group can be used for the base-reactive resin composition of the present invention as a base-reactive compound. Also, by reacting a base with a silicon compound having at least two silanol groups or alkoxysilyl groups and polycondensing the resultant silicon compound, a polymer can be obtained. Examples of the silicon compound exhibiting the polymerization reactivity is given below (compounds No. 5-1 and 5-5 have relatively low molecular weights, and compounds No. 5-2 to 5-4 are polymer).

5-1

5-2

5-3

5-4

5-5

When guanidines and phosphazen derivatives are selected as a base contained in the base proliferating agent (and/or a base generator described below) used together, a pKa falls within around 26 to 27 in acetonitrile ($CH_3CN$) solvent. For that reason, anionic ring-opening polymerization occurs, and then a monomer changes to a polymer in a chain reaction. Therefore, the base-reactive resin composition (photosensitive resin composition) containing the base proliferating agent and a base-reactive compound such as lactones and cyclic siloxanes is preferably used as a photo-curable material (UV adhesion, UV ink, UV adhesion and UV coating). Specific examples of the structure of lactones and cyclic siloxanes (compounds No. 6-1 to 6-4) as a base reactive compound, which are anionically polymerizable by guanidines and phosphazen derivatives, are shown below.

6-1

6-2

6-3

6-4

In the above embodiments, as an example of the base-reactive compounds contained in the base-reactive resin composition of the present invention, compounds No. 2-1 to

6-4 are mentioned, but the base-reactive compounds which can be used should not be limited thereto. As a base-reactive compound, any compounds which can react by the action of base to cure the composition by cross-linking, etc. can be used. Specific structures and forms of the base-reactive compound in the embodiment of the present invention can be changed to other structures and other forms in a range that the objects of the present invention can be achieved.

It is preferred embodiment to use a base generator together in the base-reactive resin composition of the present invention.

Generally, a base generator is a material producing a base by irradiation of active energy ray such as light or by heating. The base generator is used together for the base-reactive resin composition of the present invention should not be limited to any of a photobase generator and a thermal base generator (thermal potential base generator). Because the heat treatment at a high temperature is not needed for producing a base, the photobase generator is preferable.

The photobase generator is not particularly limited, but examples include o-nitrobenzyl type photobase generators, (3,5-dimethoxybenzyloxy) carbonyl type photobase generators, amyloxyimino group type photobase generators, and dihydropyridine type photobase generators. In these photobase generators, an o-nitrobenzil type photobase generator is preferably used because of excellent base generation efficiency and synthesis ease.

Examples of the o-nitrobenzyl type photobase generator include the compound represented by the following formula (21).

(21)

In formula (21), n represents an integer of 0-4. $R_1$ represents at least one substituent selected from the group consisting of an alkyl group having a carbon number of 1-18, an alkenyl group having a carbon number of 2-18, an alkynyl group having a carbon number of 2-18, an aryl group having a carbon number of 6-12, an acyl group having a carbon number of 1-18, an aroyl group having a carbon number of 7-18, a nitro group, a cyano group, an alkoxy group having a carbon number of 1-18, an alkylthio group having a carbon number of 1-18, hydroxy group and halogen atom. $R_2$ represents hydrogen atoms, an alkyl group having a carbon number of 1-18, an alkynyl group having a carbon number of 2-18, an aryl group having a carbon number of 6-12, an acyl group having a carbon number of 1-18, an aroyl group having a carbon number of 7-18, a nitro group, a cyano group, an alkoxy group having a carbon number of 1-18, an alkylthio group having a carbon number of 1-18, hydroxy group or halogen atom. X represents an amino group.

As a photobase generator, examples include the compound having the following formula (22).

(22)

In formula (22), $R_1$ represents hydrogen atom, hydroxy group, an alkoxy group, or an organic group than the aforementioned substituents. $R_2$ to $R_6$ each independently represent hydrogen atom, halogen atom, hydroxy group, an alkoxy group, a mercapto group, a sulfide group, a silyl group, a silanol group, a nitro group, a nitroso group, a cyano group, a sulfino group, sulfo group, a sulfonate group, a phosphino group, a phosphinyl group, a phosphono group, a phosphonato group, an amino group, an ammonio group or an organic group other than the aforementioned substituent. Each $R_2$ to $R_6$ plurally existing may be the same or different from each other. Two or more selected from $R_2$ to $R_6$ positioned in the same benzene ring may be connected to form a ring structure. X represents a residue obtained by removing n of hydrogen atoms from a saturated hydrocarbon including a ring structure. n represents an integer of 1-6.

Also, as a photobase generator, examples include a carboxylic acid compound represented by the following formula (a) or (b). In formula (a) or (b), X represents an oxygen atom or a sulfur atom, and B represents a base. The photobase generator represented in the following formula (a) or (b) is a carboxylate including a carboxylic acid and a base provided by decarboxylation by light irradiation.

(a)

(b)

Furthermore, as a photobase generator, examples include an oxime ester compound, an ammonium compound, a benzoin compound, a dimethoxy benzyl urethane compound, an orthonitro benzyl urethane compound disclosed in JP 2000-330270 A.

A thermal basis generator which can be used together should not be limited. Examples include trichloroacetic acid guanidine, trichloroacetic acid methylguanidine, potassium trichloroacetate, phenyl sulfonylacetic acid guanidine, p-chlorophenyl sulfonylacetic acid guanidine, p-methane sulfonyl phenyl sulfonylacetic acid guanidine, phenylpropiolic acid potassium, phenyl propiolicacid guanidine, phenylpropiolic acid cesium, p-chloro phenylpropiolic acid guanidine, p-phenylene-bis-phenylpropiolic acid guanidine, phenyl sulfonylacetic acid tetramethyl ammonium and phenylpropiolic acid tetramethyl ammonium.

As a thermal base generator, examples also include a salt of a base and an organic acid provided by decomposition by decarboxylation under heating; compounds releasing an amine by decomposition by intramolecular nucleophilic substitution reaction, Lossen rearrangement reaction or Beckman rearrangement reaction; and compounds releasing a base by some kinds of reactions under heating. Among them, the salt of a base and an organic acid provided by decomposition by decarboxylation under heating is preferably used together because of high base generation efficiency.

As a thermal base generator, examples include a salt of trichloroacetic acid disclosed in GB 998,949 B, a salt of alpha-sulfonylacetic acid disclosed in U.S. Pat. No. 4,060,420 B, a salt of propiolic acid and a derivative of 2-carboxycarboxamide disclosed in JP 59-157637 A, a salt of a base component using an organic base, an alkali metal or an alkaline earth metal and a thermal decomposable acid disclosed in JP 59-168440 A, a hydroxamic carbmate using Lossen rearrangement disclosed in JP 59-180537 A, an aldoxime carbamate generating a nitrile by heating disclosed JP 59-195237 A, thermal base generators disclosed in U.S. Pat. No. 3,220,846 B, JP 50-22625 A, JP 61-32844 A, JP 61-51139 A, JP 61-52638 A, JP 61-51140 A, JP 61-53634 A, JP 61-53640 A, JP 61-55644 A, JP 61-55645 A, and JP 2000-330270 A.

When the base proliferating agent and the base generator are used in combination for a base-reactive resin composition, it is desirable that the base forming the base proliferating agent and the base forming the base generator is common. Due to the same bases, the decomposition of the base proliferating agent is efficiently carried out.

The formulation ratio of the base proliferating agent and the base generator is from 40/1 to 5/20 (the base proliferating agent/the base generator) at a mass ratio, when the base proliferating agent and the base generator are used in combination for the base-reactive resin composition. When the formulation amounts of the base proliferating agent is too low, the base may not be effectively generated and the base-reactive compound cannot be quickly reacted. When the formulation amount of the base proliferating agent is too high, the amount of the base generator may be increased to adversely affect the solubility of the base-reactive compound in itself, and the cost may be unfavorable. The combination ratio of the base proliferating agent and the base generator preferably falls within 20/1 to 5/5 (the base proliferating agent/the base generator) at mass ratio.

When a photobase generator is used, depending on the kinds of the photobase generator and on the kinds of the base-reactive compound, a wavelength may be selected from 190-400 nm, an exposure amount may be selected from 100 to 10000 mJ/cm$^2$ relating to the irradiation light to the base-reactive resin composition (photosensitive resin composition) of the present invention. By using a sensitizing agent described below, a wavelength of light may be selected from a longer wavelength range. Irradiation time of light may be a few seconds, but generally, irradiation time may be 10 seconds or more, for example, may be 1.5 to 20 minutes, which is preferable.

When the thermal base generator is used, the heating conditions can be decided depending on kinds or amounts of the thermal base generator or kinds of the base-reactive compound contained in the base-reactive resin composition (photosensitive resin composition). For example, in general, the heating temperature may be properly selected from 50 to 150° C., and the heating time may be properly selected from 1 to 1800 minutes.

Also, when the base proliferating agent and the base-reactive compound are used in the base-reactive resin composition as main components without using a base generator, an appropriate base which the base proliferating agent can decompose may be added. The base may be preferably the same as the base of the base proliferating agent.

The content of the base proliferating agent in the base-reactive resin composition of the present invention is preferably 0.1 to 60 mass parts relative to the base-reactive compound of 100 mass parts. When the content of the base proliferating agent is less than 0.1 mass parts, quick reaction of the base-reactive compound may not be achieved. When the content of the base proliferating agent exceeds 60 mass parts, the existence of the base proliferating agent may adversely affect the solubility to the solvent of the base reactive compound. The excess content of the base proliferating agent allows the cost to be higher. The content of the base proliferating agent is more preferably 1 to 60 mass parts, further preferably 2 to 30 mass parts, more further preferably 2 to 20 mass parts and particularly preferably 2 to 15 mass parts relative to the base-reactive compound of 100 mass parts.

The base-reactive compound contained in the base-reactive resin composition of the present invention is preferably an epoxy compound (polymerizable epoxy compound) such as compounds No. 4-1 to 4-12 or the silicon compound (polymerizable silicon compounds) exhibiting polymerizable properties such as compounds No. 5-1 to 5-5. Such base-reactive resin compositions can be polymerized with the actions of light or heat to produce the polymers. Among them, the base-reactive resin composition containing the base-reactive compound initiating polymerization reaction with light (photosensitive resin composition) is preferably used.

The base-reactive resin composition of the present invention contains a thiol compound. The thiol compound works as a curing functional group for an epoxy compound, when the thiol compound is used together with the epoxy compound. Examples of the thiol compound include a polythiol compound having two or more thiol groups, for example, a polythiol compound having two to five thiol groups such as ethylene glycol bis(3-mercaptobutylate), butanediol bis(3-mercaptobutylate), dipentaerythritol hexakis(3-mercaptobutylate), ethylene glycol bis(3-mercaptoisobutylate), butanediol bis(3-mercaptoisobutylate), trimethylol propane tris(3-mercaptoisobutylate), pentaerythritol tetrakis(3-mercaptoisobutylate), dipentaerythritol hexakis(3-mercaptoisobutylate), pentaerythritol tetrakis(3-mercaptobutylate), tris[(3-mercaptopropionyloxy)ethyl] isocyanurate, pentaerythritol tetrakis(3-mercaptopropionate), trimethylol propane tris(3-mercaptopropionate), dipentaerythritol hexa(3-mercaptopropionate), diethyleneglycol bis(3-mercaptopropionate), 1,4-bis(3-mercaptobutyryloxy) butane, 1,3,5-tris(3-mercaptobutyloxyethyl)-1,3,5-triazine-2,4,6(1H,3H,5H)-trione, and pentaerythritol tetrakis(3-mercaptobuthylate). Among them, in consideration of reactivity and operatability, pentaerythritol tetrakis(3-mercaptobutylate), tris[(3-mercaptopropionyloxy)ethyl]isocyanurate or pentaerythritoltetrakis(3-mercaptopropionate) is preferably used. These thiol compounds may be used alone or in combination of two or more.

The ratio of the thiol compound relative to an epoxy compound or an oxetane compound is preferably 0.3/1.7 to 1.7/0.3 (thiol equivalent (SH equivalent)/epoxy equivalent (or an oxetane equivalent)), more preferably 0.8/1.2 to 1.2/0.8. When the ratio of the thiol equivalent/epoxy equivalent is within the above preferable range, unreacted thiol group or unreacted epoxy group (oxetane group) is inhibited from remaining in the cured product to suppress the decrease tendency of mechanical properties of the cured product.

In order to form a pattern using the base-reactive resin composition of the present invention, for example, at first, coating liquid obtained by dissolving the resin composition in an organic solvent is applied to the suitable solid surface such as a substrate and dried to form a coating. Then, the formed coating is subjected to exposure for pattern to produce a base. After that, heat treatment is conducted under the predetermined conditions to promote the polymerization reaction of the base-reactive compound contained in the base-reactive resin composition so as to cure only the exposed part. Finally, the unexposed part is dissolved by a developing solution (for example, organic solvent or base aqueous solution) to form the pattern formed of the thermal cured products. To the pattern, the heat is further conducted as needed to finish the heat curing. By the above-mentioned steps, a two-dimensional resin pattern (a general plane pattern) or a three-dimensional resin pattern (a three-dimensionally form) which is usually a negative-shaped are obtained.

When the base-reactive resin composition of the present invention is used as a photosensitive resin composition, a sensitizer can be added to enlarge an exposure wavelength region and enhance sensitivity. The usable sensitizer should not be limited. Examples include benzophenone, p,p'-tetramethyl diaminobenzophenone, p,p'-tetraethyl aminobenzophenone, 2-chlorothioxanthone, anthrone, 9-ethoxyanthracene, anthracene, pyrene, perylene, phenothiazine, benzyl, acridine orange, benzoflavin, Setoflavin-T, 9,10-diphenylanthracene, 9-fluorenone, acetophenone, phenanthrene, 2-nitrofluorene, 5-nitro acenaphthene, benzoquinone, 2-chloro-4-nitroaniline, N-acetyl-p-nitroaniline, p-nitroaniline, N-acetyl-4-nitro-1-naphthylamine, picramide, anthraquinone, 2-ethylanthraquinone, 2-tert-butyl anthraquinone, 1,2-benzanthraquinone, 3-methyl-1,3-diaza-1,9-benz anthrone, dibenzal acetone, 1,2-naphthoquinone, 3,3'-carbonyl-bis (5,7-dimethoxycarbonyl coumarin) and coronene. The sensitizer may be used alone, or in combination of two or more.

When the base-reactive resin composition of the present invention is used as a photosensitive resin composition, the amount of the sensitizer is appropriately determined depending on the photobase generator, the base-reactive compound and the required sensitivity, etc., but is preferably in the range of 1 to 30% by mass to the entire base-reactive resin composition. When the addition amount of the sensitizer is less than 1% by mass, the sensitivity may not be enhanced sufficiently. When the addition amount of the sensitizer is more than 30% by mass, the addition amount of the sensitizer may be excessive. The addition amount of the sensitizer is more preferably in the range of 5 to 20% by mass to the entire base-reactive resin composition.

When the base-reactive resin composition of the present invention is applied to the base material, solvent can be added if necessary. The addition of solvent to the base-reactive resin composition can enhance the application property resulting in improved workability. The solvent to be used is not limited particularly, examples include aromatic hydrocarbons such as benzene, xylene, toluene, ethylbenzene, styrene, trimethylbenzene and diethylbenzene; saturated or unsaturated hydrocarbons such as cyclohexane, cyclohexene, dipentene, n-pentane, isopentane, n-hexane, isohexane, n-heptane, isoheptane, n-octane, isooctane, n-nonane, isononane, n-decane, isodecane, tetrahydronaphthalene and squalene; ethers such as diethyl ether, di-n-propyl ether, di-isopropyl ether, dibutyl ether, ethyl propyl ether, diphenyl ether, diethylene glycol dimethyl ether, diethylene glycol diethyl ether, diethylene glycol dibutyl ether, diethylene glycol methyl ethyl ether, dipropylene glycol dimethyl ether, dipropylene glycol diethyl ether, dipropylene glycol dibutyl ether, dipropylene glycol methyl ethyl ether, ethylene glycol dimethyl ether, ethylene glycol diethyl ether, ethylene glycol dipropyl ether, ethylene glycol methyl ethyl ether, tetrahydrofuran, 1,4-dioxane, propylene glycol monomethyl ether acetate, ethylene glycol monoethyl ether acetate, dipropylene glycol methyl ether acetate, diethylene glycol monoethyl ether acetate, ethyl cyclohexane, methyl cyclohexane, p-menthane, o-menthane, m-menthane, dipropyl ether and dibutyl ether; ketones such as acetone, methyl ethyl ketone, methyl isobutyl ketone, diethyl ketone, dipropyl ketone, methyl amyl ketone, cyclopentanone, cyclohexanone and cycloheptanone and esters such as ethylacetate, methylacetate, butylacetate, propylacetate, cyclohexylacetate, methylacetate cellosolve, ethylacetate cellosolve, butylacetate cellosolve, ethyllactate, propyllactate, butyllactate, isoamyllactate and stearic acid butylstearate. Those solvent may be used alone or in combination of two or more.

The solvent content in the base-reactive resin composition of the present invention is not limited particularly. For example, the solvent content is appropriately selected so that the base-reactive resin composition can be applied uniformly when the base-reactive resin composition is applied on the given base material to form film.

The additive may be appropriately added to the base-reactive resin composition of the present invention as long as the additive do not disturb the object and effect of the present invention. The usable additive include filler, pigment, dye, leveling agent, defoaming agent, antistatic agent, ultraviolet absorbent, pH regulator, dispersant, dispersant assistant, surface-modifying agent, plasticizer, plasticization accelerator, drip preventing agent, and curing accelerator. Those additives may be used alone or in combination of two or more.

The base-reactive resin composition of the present invention explained above is excellent in curing rate and in reaction efficiency, because the reaction of the base generated from the base proliferating agent with an epoxy compound progresses in chains. Therefore, the base-reactive resin composition of the present invention can be suitably used for, for example, a high sensitivity photocurable material and a resist material (pattern-forming material) etc.

A cured product of the base-reactive resin composition of the present invention is widely used in the fields requiring properties such as heat resistance, dimensional stability and insulation, for example, as a paint, a printing ink, a color filter, a film for flexible display, a semiconductor device, an electronic part, an interlayer insulating film, a wiring coating film, a light circuit, a light circuit component, an anti-reflection coat, a hologram, an optical part, and a constitution part for a construction material.

The embodiment explained above shows one embodiment of the present invention and the present invention is not limited to the embodiment mentioned above. It goes without saying that when configuration of the present invention is satisfied and the object and the effect of the present invention are achieved, the present invention includes modification and improvement. It is not a problem that the specific structures and the specific forms etc., of the present invention can be made to be different structure and form etc., as long as the object and the effect of the present invention is achieved. The present invention is not limited to each embodiment mentioned above and includes modification and improvement as long as the object and the effect of the present invention are achieved.

EXAMPLES

The present invention now will be described in more detail with reference to Examples, but these Examples are not intended to limit the present invention by any means.

Example 1 Synthesis of Base Proliferating Agent Represented by Formula (1) of the Present Invention 3.1 parts of 4-aminopyridine was dissolved in 10.7 parts of DMSO. Subsequently 4.0 parts of chloroformic acid 9-fluorenylmethyl represented by formula (30) was added dropwise to the solution. Then the mixture was stirred at room temperature for 3 hours and the reaction was carried out. After the reaction, the mixture was washed at 40° C. by adding 25 parts of toluene and 25 parts of water, and toluene solution was separated by a separating funnel and collected. The operation was repeated three times. The obtained toluene solution was cooled to 3° C. and precipitated crystals were collected by suction filtration to obtain 3.8 parts of the compound (the base proliferating agent of the present invention) represented by formula (31).

(30)

(31)

Examples 2 to 3 and Comparative Examples 1 to 4 Preparation of Base-Reactive Resin Composition Respective components were mixed in accordance with the amounts (parts by mass) listed in Table 1. The obtained mixture was ground in a mortar to make uniform dispersion, and then the mixture was subjected to kneading and deaeration by VMX-360 manufactured by EME CORP. for 3 minutes respectively. The base-reactive resin compositions of the Examples and the Comparative Examples were prepared.

(Evaluation of Change in Viscoelasticity of Base-Reactive Resin Composition)

Figure 1:
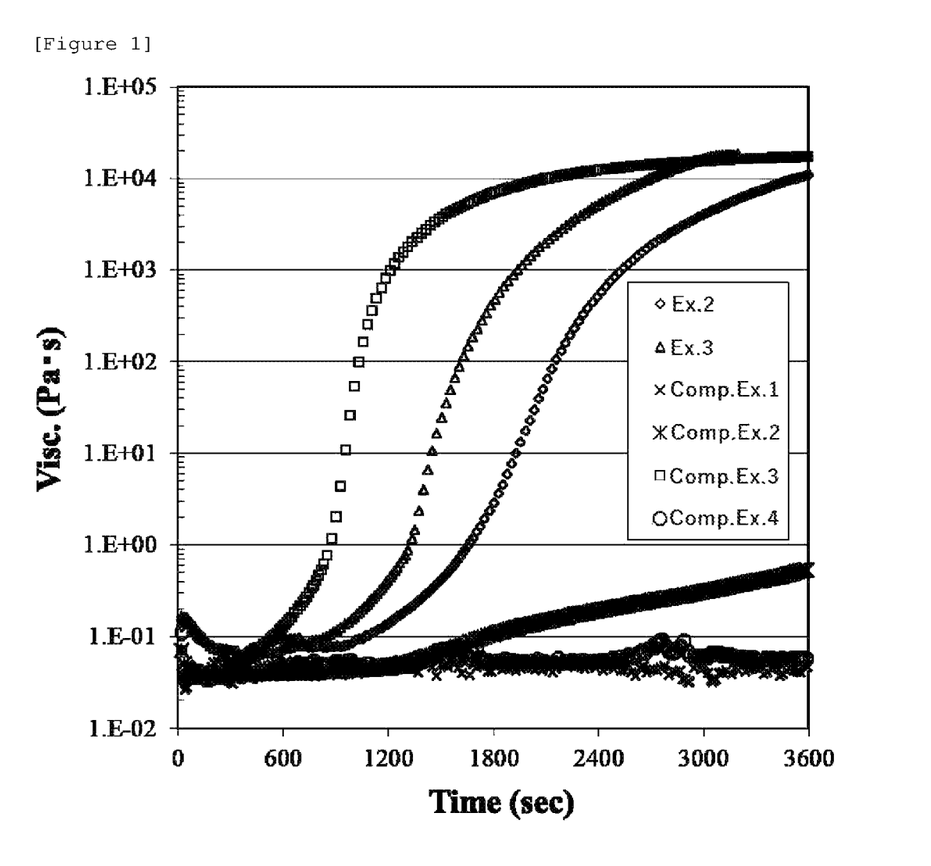
FIG. 1 shows the measurement results of viscoelasticity of the base-reactive resin compositions of the Examples and the Comparative Examples.

The base-reactive resin compositions obtained in Examples 2 and 3 and Comparative Examples 1 to 4 were kept at 100° C. for 1 hour and the change in viscoelasticity of the base-reactive resin compositions was measured by Discovery HR-3 manufactured by TA instrument Japan Inc. The results are shown in FIG. 1. Based on measurement results in FIG. 1, the time until a viscosity reaches $1.0 \times 10^2$ Pa·s is described as an evaluation index in Table 1.

TABLE 1

Composition Ratio and Evaluation Resluts of Base-Reactive Resin Composition

| | | Example 2 | Example 3 | Comparative Example 1 | Comparative Example 2 | Comparative Example 3 | Comparative Example 4 |
|---|---|---|---|---|---|---|---|
| Composition | A-1 | 0.0872 | 0.0872 | | | | |
| | A-2 | | 0.0175 | 0.0175 | | | |
| | A-3 | | | | 0.03 | | |
| | A-4 | | | | | 0.026 | |
| | A-5 | | | | | | 0.026 |
| | Epoxy resin | | | | 5.1 | | |
| | Silica particles | | | | 0.05 | | |
| Evaluation Results | Time (Sec) | 2111 | 1581 | — | — | 1032 | — |

A-1: Base-proliferating agent obtained in Example 1
A-2: Triethylamine
A-3: 2-Ethyl-4-methyl-imidazole (2E4MZ)
A-4: 4-Aminopyridine
A-5: 3-Aminopyridine
Epoxy resin: jER828 (produced by Mitsubishi Chemical Corporation)
Silica particles: X-24-9103A (produced by Shin-Etsu Chemical Co., Ltd.)
In the above table, the symbol "—" is meant to be that the viscosity did not reach $1.0 \times 10^2$ Pa · s in 1 hour.

(Evaluation of Storage Stability of Base-Reactive Resin Composition)

Figure 2:
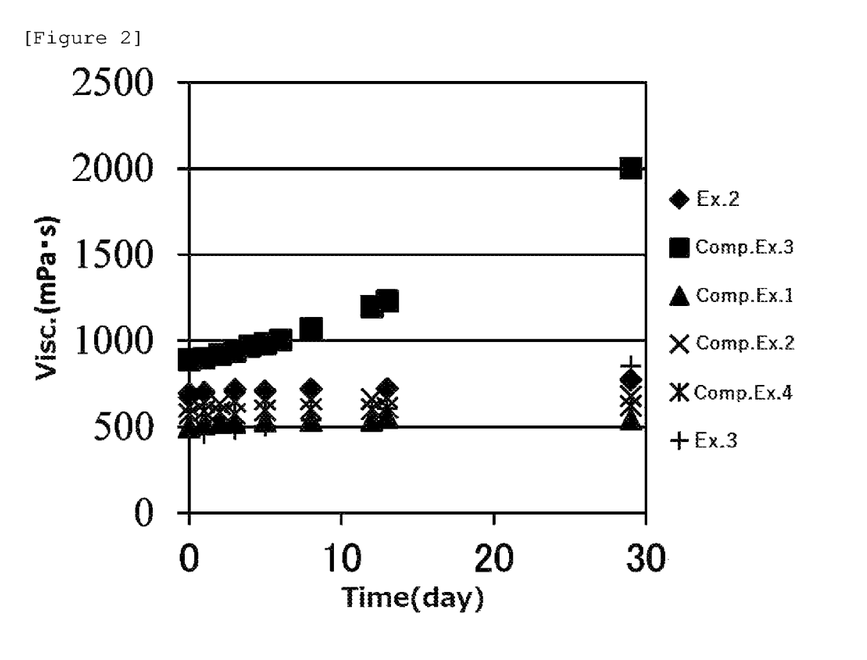
FIG. 2 shows the results of temporal change of the base-reactive resin compositions of the Examples and the Comparative Examples.

The base-reactive resin composition obtained in Examples 2 and 3 and Comparative Examples 1 to 4 were left in an oven (DNE400 manufactured by Yamato Scientific Co., ltd.) as 35° C. The change in the viscosity with time was measured by a viscometer (TV-20 manufactured by Touki-Sangyo Co., Ltd.) to evaluate the storage stability. The results are shown in FIG. 2. It is confirmed that compared to Comparative Example 3 using 4-aminopyridine, the base-reactive resin compositions of the present invention are excellent in storage stability.

Because as shown in Table 1, the curing of epoxy resin by using 4-aminopyridine progress rapidly at a low temperature compared to an imidazole derivative used for curing of epoxy resin generally, 4-aminopyridine works as an excellent curing agent. However, the curing rate is so high that the reaction control is difficult when mixing with an epoxy resin (Comparative Example 3). On the other hand, when mixing the compound represented by formula (1) or (2) of the present invention with an epoxy resin, the time until the curing is finished can be prolonged while keeping the reaction rate. Furthermore, when the amine working as trigger is added to the compound represented by formula (1) or (2) of the present invention, the base proliferating reaction progresses. Therefore, the curing time can be shortened. This shows for example that the curing time can be controlled when the photobase generator is used.

INDUSTRIAL APPLICABILITY

The base proliferating agent represented by formula (1) or (2) of the present invention obtained by derivatizing aminopyridines and setting it to a latent state can be used, for example, for the cross-linking reaction of epoxy resin compounds etc., and also can be suitably used for the base-reactive resin composition which is curable by the action of light or heat, because the base proliferating reaction generating new bases progresses efficiently in the presence of base.

The invention claimed is:

1. A thermally curable resin composition comprising a base proliferating agent represented by formula (1) or (2):

(1)

wherein in formula (1), $R_1$, $R_2$ and $R_3$ are each independently a hydrogen atom or a substituent, and n is each independently an integer of 1 to 4, (2)

wherein in formula (2), $R_4$ is each independently a hydrogen atom, an alkyl group having a carbon number of 1 to 6, an aryl group having a carbon number of 6 to 12, a halogen atom, a nitro group, a nitroso group or a cyano group, or $R_4$ is connected to each other to form a ring; $R_5$ is each independently a hydrogen atom or an alkyl group having a carbon number of 1 to 6; and $R_6$ is a hydrogen atom or a substituent, and n is each independently an integer of 1 to 4.

2. The thermally curable resin composition according to claim 1, wherein in formula (1) and (2), each of $R_1$ and $R_4$ is independently a hydrogen atom, an alkyl group having a carbon number of 1 to 6, a halogen atom, a nitro group, a nitroso group, or a cyano group, or each of $R_1$ and $R_4$ is connected to each other to form a ring; wherein each of $R_2$ and $R_5$ is independently a hydrogen atom or an alkyl group having a carbon number of 1-6; and wherein each of $R_3$ and $R_6$ is independently a hydrogen atom or an alkyl group having a carbon number of 1 to 6.

3. The thermally curable resin composition according to claim 2, further comprising an epoxy resin.

4. The thermally curable resin composition according to claim 1, further comprising an epoxy resin.

* * * * *

UNITED STATES PATENT AND TRADEMARK OFFICE
CERTIFICATE OF CORRECTION

PATENT NO. : 11,905,361 B2
APPLICATION NO. : 17/851401
DATED : February 20, 2024
INVENTOR(S) : Kiwamu Terada et al.

It is certified that error appears in the above-identified patent and that said Letters Patent is hereby corrected as shown below:

In the Claims

Column 26, Line 24, Claim 1, delete "group" and insert -- group, --

Signed and Sealed this
Sixteenth Day of April, 2024

Katherine Kelly Vidal
*Director of the United States Patent and Trademark Office*